United States Patent [19]

Poetzschke et al.

[11] Patent Number: 4,572,735
[45] Date of Patent: Feb. 25, 1986

[54] PROCESS FOR SORTING METAL PARTICLES

[75] Inventors: Manfred Poetzschke, Kronberg; Hans-Peter Sattler, Bad Homburg, both of Fed. Rep. of Germany

[73] Assignees: Metallgesellschaft Aktiengesellschaft; Eumet Metallaufbereitungsgesellschaft mbH & Co., both of Frankfurt, Fed. Rep. of Germany; RTZ Ore Sorters (North America) Inc., Alpharetta, Ga.

[21] Appl. No.: 577,951

[22] Filed: Feb. 8, 1984

[30] Foreign Application Priority Data

Feb. 12, 1983 [DE] Fed. Rep. of Germany ....... 3304850

[51] Int. Cl.⁴ ............................................... C22B 7/00
[52] U.S. Cl. ...................................... 75/10 R; 75/63; 75/68 R; 209/3.1; 241/24

[58] Field of Search ................. 75/63, 10 R, 68 R; 241/24; 209/3.1, 576, 587

[56] References Cited

U.S. PATENT DOCUMENTS 4,301,928  11/1981  Coccia ................................ 209/587
4,317,521   3/1982  Clark et al. ........................ 209/589
4,363,722  12/1982  Dresty, Jr. et al. ................. 241/24

Primary Examiner—Melvyn J. Andrews
Attorney, Agent, or Firm—Sprung Horn Kramer & Woods

[57] ABSTRACT

In the proposed process of sorting metal particles in dependence on their chemical composition the melting point and/or the melting temperature range are used to identify the particles. A radiation pyrometer integrally combined with a laser is used for this purpose and only a fraction of a second is required to test a given particle. A graph shows the melting temperatures of the metals and alloys frequently occurring in shredded scrap.

11 Claims, 1 Drawing Figure

PROCESS FOR SORTING METAL PARTICLES

BACKGROUND OF THE INVENTION

1. Field of the Invention

This invention relates to a process of dividing a stream of metal particles differing in chemical composition into partial streams of metal particles having the same chemical composition in that the particles are singled and irradiated with electromagnetic waves, the reflected radiation is analyzed and a sorting device is controlled to change the path for each metal particle in dependence on the results of the analysis.

2. Discussion of Prior Art

Particles differing in chemical composition can be sorted by a number of known processes in which a stream of singled particles is moved past a radiant source and is irradiated and the reflected radiation is measured and used to identify the kind of particle.

In a process proposed by U.S. Pat. No. 4,212,397, diamonds are separated from the accompanying materials, a fluoresence of the stream of particles is excited by X-rays, the decay time is measured photoelectrically, and the results are delivered to a sorting logic for controlling mechanical or pneumatic diverting means.

German Offenlegungsschrift No. 30 47 536 discloses a process in which particles derived from scrap and consisting of various metals and of various alloys are exposed to X-rays or isotope radiation and the reflected radiation is measured and used to identification.

A similar process of sorting metal scrap is known from *New Scientist*, 63, (1982), page 490.

*Engineering and Mining Journal* 183, (1982, 8) describes on pages 72 to 75 a process for enriching ores, which are irradiated from two radio-active sources having different energy levels, whereafter the scattered gamma radiation is used to distinguish the particles.

The processes mentioned above can be used in part only for certain kinds of particles or have the basic disadvantage that they cannot be used in a field which is increasing in significance, namely, the recovery of the nonferrous metal fractions of scrap. This is due to the fact that most of the particles obtained in that case have been subjected to a surface treatment or provided with a surface coating so that the results of measurement are distorted and, as a result, the yield is not satisfactory.

For this reason, it is an object of this invention to provide a sorting process which is based on the principle of the known process and in which the surface finish of the metal particles is no longer significant, i.e., a process for separating metal particles regardless of their surface finish. In other words, a process is desired in which the nature of the core of each particle is detected and the particles can be sorted with high qualitative and quantitative yields.

In a process of the kind described first hereinbefore, this object is accomplished in that the melting point and/or the melting temperature range of the metal particle is used as a criterion for the distinction between the metal particles. For this purpose, the metal particles are spot-fused by means of a laser beam and the temperature profile is measured by means of a radiation pyrometer and is electronically analyzed. The melting temperature range is suitably used as a criterion for a fine sorting of alloys which contain the same base metal. A predetermined temperature interval or the energy consumption of the laser can be used as a criterion in determining the melting temperature range. The process according to the invention is preferably applied to shredded scrap from which non-metallic and ferromagnetic constituents have already been separated.

A radiation pyrometer integrally combined with a laser is suitable used to carry out the process. Such a system has been described in *Temperature* 5 (1982) on pages 439 to 446. On the surface of each particle a spot which is, e.g., 1 mm in diameter is heated to fusion by a pulsed laser beam and the temperature is measured at the same time. The melting point or the lower end of the melting temperature range has been reached when the temperature does not rise further in spite of an additional supply of energy. The temperature which is then measured can be used to identify the particle.

By such systems, the melting and the measurement can be effected within a fraction of a second so that the measurement is not significantly affected by the movement of the particle. Such processes can be considered as being economical when at least 10 particles can be identified per second. Singling and sorting means operating at high speed must be used for that purpose.

The economy of the process can be increased further in that the velocity of the stream of particles is increased because stationary testing means are replaced by testing means which move with the stream of particles at least for the duration of each measurement so that the relative velocity between the testing means and the object being tested is zero or negligibly small. If the stream of particles advances along a straight line, the testing device can be reciprocated along a straight line so that a new particle is tested during each forward stroke, or one or more testing devices may revolve around an orbit in synchronism with the stream of the singled particles.

Figure 1:
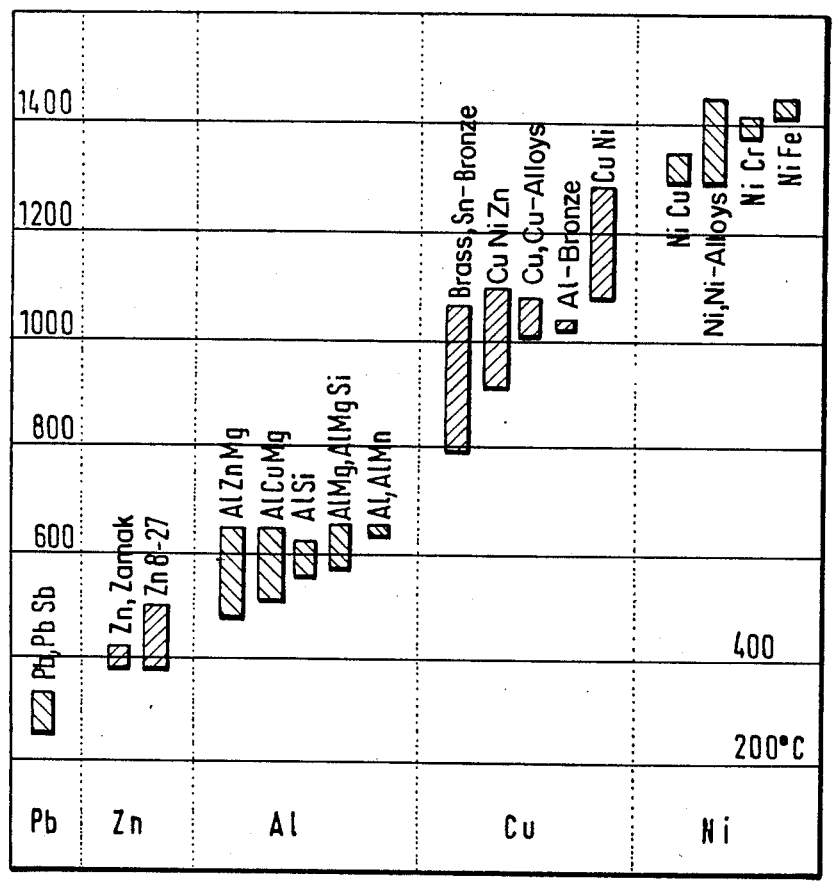
FIG. 1 is a diagram of the melting points of the important non-ferrous metals and alloys found in scrap.

In the accompanying diagrams the melting points of the most important non-ferrous metals and non-ferrous alloys found in scraps are plotted. It is apparent that the melting point can advantageously be used for identification with good accuracy. The process according to the invention can be carried out in a more sophisticated manner in that the lower and upper limits of the melting temperature range are detected. This practice permits of a detection of another characteristic property and of a sorting of the alloys which are typical for a given group of alloys. For instance, scrap aluminum can be sorted for the groups of alloys stated in the diagram by a combination of the parameters "melting point" and "melting temperature range".

The discontinuous change of the emission coefficient can be used as an indication that the melting point has been reached if such change is characteristic of the metal particles and can be detected with adequate reliability by measurement.

In practice the invention is used for identifying and sorting mixed die casting scrap containing the zinc alloy ZnAl4Cu1 (Zamak-ASTM Type A C41 A) and the aluminum alloys AlSi12 and AlSi8Cu3 (comparable with AA No. 413,0 and B 380,0).

The machine-singled scrap particles are spot-fused by means of a laser beam generated by a 400 Watt $CO_2$ laser as used for cutting metals. The laser beam is focused in the centre of the 3.5 mm diameter measuring spot of an infrared pyrometer with a measuring range from 300° C. to 750° C. and a measuring time of less than 3 milliseconds. The pyrometer is equipped with a test value storage unit, optional for maximal or ultimate value reading. The ultimate reading of the temperature is used to indicate the melting point respectively the beginning of the melting range of the alloys (380°–390° C. for ZnAl4Cu1; 510°–600° C. for AlSi8Cu3; 575°–585° C. for AlSi12). The identification of the melting temperature by ultimate value reading is possible because of the abrupt change of the emission coefficient of the alloys during melting which causes a breakdown of the pyrometer measurement.

What is claimed is:

1. In a process of sorting metal or metal alloy particles of different composition, wherein the particles are singled and conveyed, the improvement comprising partially melting the particles and measuring the melting temperature while the particles are being conveyed and sorting the particles on the basis of the melting temperature corresponding thereto.

2. A process according to claim 1, wherein the metal or metal alloy particles are partially melted by spot-fusing by means of a laser beam and the temperature profile is measured by means of a radiation pyrometer.

3. A process according to claim 2, wherein a predetermined temperature interval is used in determining a melting temperature range.

4. A process according to claim 2, wherein the energy consumption of the laser is used in determining a melting temperature range.

5. A process according to claim 1, wherein said metal or alloy particles comprise shredded scrap.

6. A process according to claim 5, wherein said scrap comprises non-metallic and ferromagnetic constituents and wherein the non-metallic and ferromagnetic constituents are removed prior to the partial melting.

7. A process according to claim 5, wherein said scrap comprises non-ferrous metal or metal alloy particles.

8. A process according to claim 1, wherein scrap aluminum containing particles are separated.

9. A process according to claim 8, wherein scrap aluminum particles are separated from zinc containing particles.

10. A process according to claim 8, wherein scrap aluminum particles are separated from copper containing particles.

11. A process according to claim 8, wherein scrap aluminum particles are separated from nickel containing particles.

* * * * *